United States Patent [19]

Viebach et al.

[11] Patent Number: 5,152,289
[45] Date of Patent: Oct. 6, 1992

[54] TRANSDUCER KINEMATICS IN LITHOTRIPTERS

[75] Inventors: Thomas Viebach, Paehl; Peter Buchbauer, Garching; Bernhard Herrmann, Germering, all of Fed. Rep. of Germany

[73] Assignee: Dornier Medizintechnik GmbH, Fed. Rep. of Germany

[21] Appl. No.: 513,612

[22] Filed: Apr. 24, 1990

[30] Foreign Application Priority Data

May 11, 1989 [DE] Fed. Rep. of Germany ....... 3915384

[51] Int. Cl.⁵ .............................................. A61B 17/22
[52] U.S. Cl. ............................ 128/660.03; 128/24 EL
[58] Field of Search ........... 128/660.03, 24 EL, 24 A, 128/804

[56] References Cited

U.S. PATENT DOCUMENTS

| | | | |
|---|---|---|---|
| 4,669,483 | 6/1987 | Hepp et al. | 128/24 EL |
| 4,821,730 | 4/1989 | Wurster et al. | 128/24 EL |
| 4,844,079 | 7/1989 | Naser et al. | 128/24 EL |
| 4,913,156 | 4/1990 | Inbar et al. | 128/660.03 |

FOREIGN PATENT DOCUMENTS 0316863 5/1989 European Pat. Off. ....... 128/24 FL

Primary Examiner—Ruth S. Smith
Attorney, Agent, or Firm—R. H. Siegemund

[57] ABSTRACT

A lithotripter includes a therapeutic head provided with a source for focusing shockwaves in a focal point on a first axis; an ultrasonic transducer having an axis for imaging an area in a patient in which shockwaves are to be focussed is connected to the therapeutic head for movement in relation to the head in isocentric relation to that focal point such that two axes intersect in that focal point, independently form a variable angular orientation of the axes to each other.

5 Claims, 2 Drawing Sheets

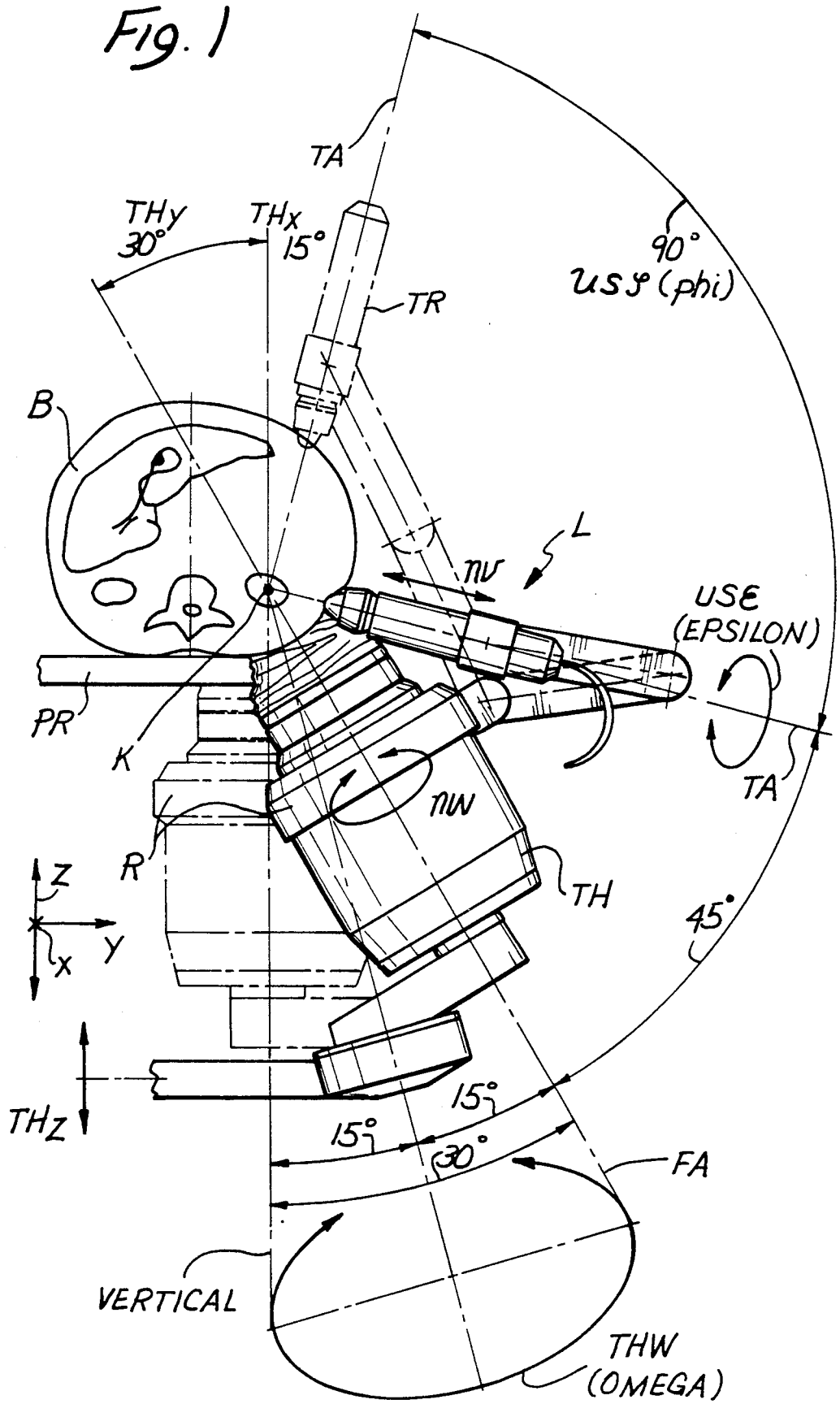

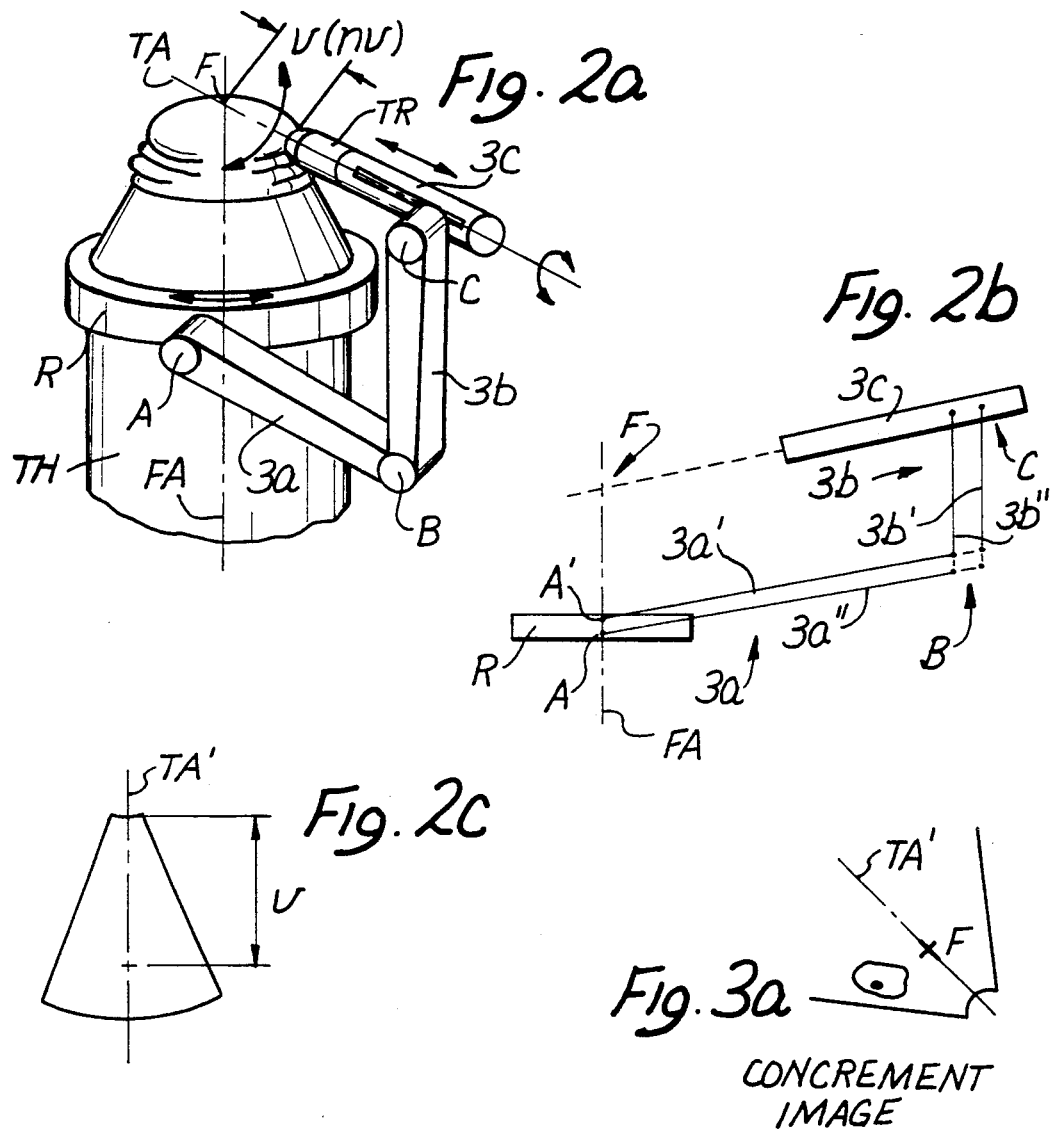
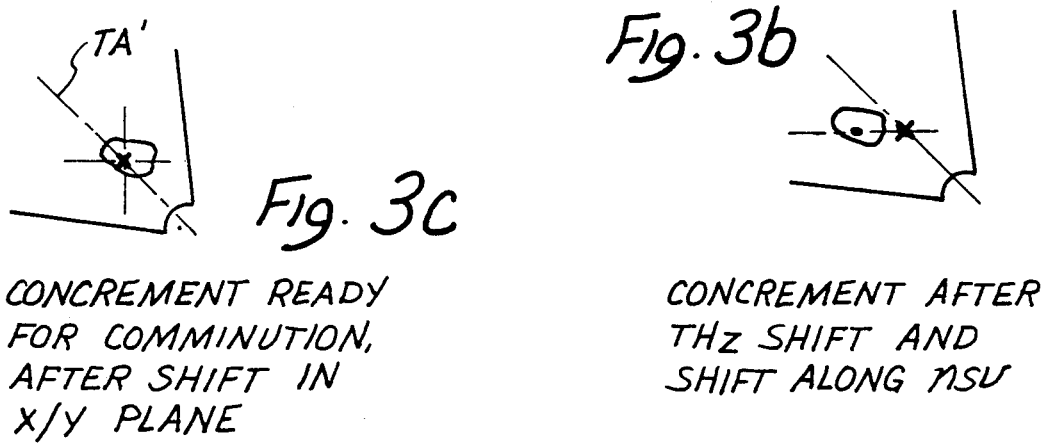
CONCREMENT READY FOR COMMINUTION, AFTER SHIFT IN X/Y PLANE
CONCREMENT AFTER THz SHIFT AND SHIFT ALONG nsv

TRANSDUCER KINEMATICS IN LITHOTRIPTERS

BACKGROUND OF THE INVENTION

The present invention relates to a device and apparatus for locating concrements in the body of a human being and for targetting these concrements in conjunction with a lithotripter that destroys them and wherein an ultrasonic transducer is controlled as to its motion and position such that its center axis is always oriented towards a particular point, this property can also be described as isocentrism.

Lithotripters are known wherein a shockwave source is positioned to be fixed as to its spatial coordinates and the patient is shifted until the particular body part to be treated is in fact correctly positioned in relation to the focal area of the shockwave source. In other configurations of the equipment the shockwave source is movable possibly in addition to the patient's rest whereby the shockwave source is positioned in a device that could be called a therapeutic head, and suitable structure is provided in relation to that head to obtain focusing and proper conduction of the shockwave for them to be focused in the patient.

The U.S. Pat. No. 4,669,483 of common assignee discloses a positioning device including an ultrasonic transducer that is oriented always in an isocentric fashion. The device disclosed in that patent is basically of a sound configuration but the mechanical structure is rather involved and relatively cumbersome.

DESCRIPTION OF THE INVENTION

It is an object of the present invention to provide a new and improved positioning structure with locating kinematics for a lithotripter which is simpler as compared with the prior art structure and particularly facilitates positioning as well as locating of concrements.

It is therefore a specific object of the present invention to provide a new and improved apparatus for locating concrements in the body of the patient in conjunction with the lithotripter and the ultrasonic locating source which is to be controlled in an isocentric fashion as defined above.

In accordance with the preferred embodiment of the invention it is is suggested to connect an ultrasonic transducer on a movable therapeutic head which contains and includes structure and equipment for the production, focussing and conducting of focussed shockwaves into the body of a patient. The transducer moves isocentrically in relation to the focus of the therapeutic head.

In other words the ultrasonic transducer is connected in relation to the therapeutic head that contains the shockwave generator such that the ultrasonic transducer though movable is always oriented and aims towards the focus of the shockwave generator. The above mentioned U.S. Pat. No. 4,669,483 provides for correlation between an isocenter of the transducer on one hand and the focal point of the shockwave source on the other hand. This correlation and the relative movement and coordination of positioning is no longer necessary. The two points are found to coincide. Hence the attending physician is free in his selection of the observation window or of the treatment window and he still can find and locate the concrement very rapidly and position the patient in relation to the therapeutic head so that efficiently and safely a comminution of the concrement so found can obtain.

In accordance with the configuration the transducer is mounted on an annulus or ring which loops around the therapeutic head and has an axis of rotation that coincides with the center axis of the therapeutic head. That head if constructed for focusing of generated shockwaves has an axis defined for example by a line that is determined by the two focal points of a rotational ellipsoid. One of these focal points is situated inside the reflector and coincides with the point of shock wave generation; the other focal point is the operating focus into which the shock waves generated in the head are focussed. The transducer is now guided kinematically to use the second focus as isocenter whereby three levers are used. The first and the third lever are interconnected and related for example such that they run always parallel in relation to each other; a second lever interconnects the first and the third one, the first one being additionally connected to the ring, the third one to the transducer. In addition the transducer should be capable of turning around its own longitudinal axis and/or there should be a shift along that axis which provides additional degrees of freedom as far as selecting a suitable window by the doctor is concerned. The term "window" is actually a metaphorical designation for a suitable skin area of the patient through which the yet unfocused but converging shockwaves are focused.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 illustrates a first example in accordance with the preferred embodiment of the present invention showing the locating kinematics as proposed here;

FIG. 2a illustrates a certain part of FIG. 1 in greater detail and in perspective view;

FIG. 2b is a kinematic representation of structure for obtaining isocentrism;

FIG. 2c is a schematic imaging diagram associated with illustration of FIG. 2a; and FIGS. 3a,b,c are respectively three ultrasonic images which on one hand are obtainable by means of the ultrasonic locating transducer of the equipment while on the other hand the figures facilitate the description of the invention as far as the procedure of locating is concerned.

Proceeding now to the detailed description of the drawings, FIG. 1 illustrates somewhat schematically a cross section through the body B of a patient having a kidney K and there is a kidney stone within the kidney. A point identified by the letter F is situated in the kidney stone. The significance of point F will be explained shortly. The patient basically rests on a rest PR which is schematically indicated and in relation thereto is provided a therapeutic head TH. This head TH contains the lithotripter equipment proper i.e. structure and devices for the production of focussed shockwaves and for the conduction of these shockwaves as they converge towards a focal point. As far as the patient rest PR is concerned please refer to copending applications; Ser. No. 513,611 filed Apr. 24, 1990 and Ser. No.

513,613 filed Apr. 24, 1990 whose content is incorporated by the reference.

It is necessary in general to provide this head in a specific spatial relationship to the body B generally and to the kidney stone in particular. The therapeutic head is for example constructed to be a rotational ellipsoid, which has two focal points. A spark discharge in one focal point produces a shockwave which is reflected by the ellipsoid and refocused thereby into a focal point and is identified by F. That focal point is external to the head TH and is to coincide with the concrement to be comminuted. Different shockwave generators can be used, but they all are to establish a focal point into which shockwaves are focused. That focal point F, together with the point or center of shockwave production, defines an axis FA of symmetry of head TH.

An ultrasonic transducer TR is mounted to the head TH in a manner to be described. Transducer TR has a number of purposes. (i) the transducer provides an ultrasonic image; (ii) that image is provided in such a manner that a particular point is kept in the center of the image as an invariant reference, the invariance being effective irrespective of the orientation of the axis TA; (iii) that point of invariance as so imaged represents a point external to the transducer, and it will be shown that that particular point coincides with the focal point F of the lithotripter.

In this specific configuration transducer TR is connected to the head TH by means of the following structure. That mounting structure includes a ring R and a lever linkage L that connects the transducer TR to the head TH in such a manner that the axis TA of the therapeutic head runs through the point F. A variety of different interconnections of levers and guiding structures in relation to ring R is provided which enforces this relation. FIGS. 2a and 2b in particular show a structure that maintains geometric isocentrism in relation to the point F.

The ring R is provided and mounted for rotation about the center axis FA of the head TH. Three levers or sets of levers 3a, 3b and 3c are provided and connected to the ring R. These levers guide, orient and position the transducer TR. They have to accommodate one basic movement, namely pivoting transducer TR about point F for an angle US phi. Three further motions of transducer TR do not affect its orientation vis-a-vis F. One motion is UV, that is along axis TA, i.e. towards or away from point F, without interfering with the intersection of axis TA with point F. A third transducer motion is US epsilon, that is also an angular motion of the transducer TR about its own axis TA which is angle US omega. Still another motion is that of ring R about its center axis FA which leaves invariant the orientation of transducer axis TA on point F, the transducer TR is still directed to point F. Point F is, therefore, as far as the equipment is concerned the invariant focal point of the shockwave source and lithotripter in the head TH, on which point the transducer TR is trained in that transducer TR is isocentrically positioned and positionable to the focal point F.

The following motions of the head TH itself are possible. There is a bidirectional shift THZ of the head, basically in up and down direction. TH omega is an angle about which the therapeutic head TH is turned on a cone with an apex in point F. This turning results in deflections with respect to the x and y axes. The x axis runs horizontally transversely to the vertical or z axis as well as the plane of the drawing, and the y axis is horizontal in the plane of the drawing of FIG. 1. As a consequence, there is a deflection THy only in the positive y-direction, with a maximum angular deflection in the z-y plane (that is the drawing) of 30 degrees, while in the transverse, z-x plane, the deflection THx is by $+x$ and $-x$, with $+15$ degrees and $-15$ degrees being the maxima. The deflection talked about is of course delineated by the axis FA of the head TH. It can be seen, that the axis FA will run straight down in the vertical ($y=0$, $x=0$) after a 180 degrees turn as compared with the maximum deflection in the positive y-direction that is illustrated in FIG. 1. The significance of these relations is further elaborated in one copending application of common assignee Ser. No. 513,613, supra, the content of which is incorporated by reference.

In the particular configuration owing to the movement of the transducer TR in and along its longitudinal axis TA its portion can be acquired electronically in terms of displacement data, and the disposition of the therapeutic focus F will be indicated in the ultrasonic image as an invariant point. Since the motion of the transducer TR as stated is always isocentric with regard to focal point F that point is therefore always visible as a center point in the ultrasonic image and on the image of axis TA. Please note that isocentricity is retained even if the head TH moves with its axis FA on a cone as described.

Further details are now shown in FIG. 2a as far as the positioning kinematics of the transducer is concerned in relation to the therapeutic head TH. The ring R and the three levers 3a,b,c position the transducer TR. The ring R as stated can be turned around the therapeutic head TH on its axis FA. The three levers have turning or pivot axes A,B,C respectively and the arrows show the motion the transducer TR may undergo.

Back to FIG. 1 there is shown a double arrow USnu delineating possible motion of the transducer TR along its own longitudinal axis TA; a swivel motion of the transducer TR is permitted by angle US phi and about an axis transverse to the cone defining axis FA. FIG. 2c shows the usual ultrasonic sector scan image, and the spacing or distance nu is also indicated in FIG. 2a may be visibly marked in the image that is produced by the ultrasonic transducer. The head TR may also turn around its own axis (US epsilon). In addition there can be further a swiveling transducer TR around the longitudinal axis TA of the therapeutic head TH as the ring R is turned (US omega).

The positioning and locating of a concrement by means of the ultrasonic transducer TR obtains for positioning the therapeutic head TH in relation to the patient and his/her body B. The possibilities of movement are imparted upon the transducer TR by the mechanical structure as described and are specifically characterized in that the central axis TA (imaged TA') and which is the axis of symmetry of the ultrasonic image, will always run through the focus F of the therapeutic head TH.

The distance nu of the transducer TR in relation to the focus F is variable and will be indicated representatively on the center axis of the ultrasonic image. By means of this arrangement the doctor locates the concrement and maintains its position, while observing the result of the comminution process. The transducer TR and the head TH can be positioned and repositioned and changed in its position over a large range of degrees of freedom in relation to the patient. This may be necessary in order to provide, in accordance with experience of the attending physican, a well positioned "window" through which to launch the shockwaves. This repositioning will always be carried out with the clear understanding that the focal point F remains invariant throughout as reference point.

The three levers 3a,b,c (or sets of levers) respectively pivot around axes and pivot points A,B,C (or sets of points). These motions are interconnected through appropriate transmission elements such as to other belts, gears, chains, thrust rods or the like and they are inside of the hinge lever structure as illustrated. This way there is a full way articulation and all of these elements can in fact undergo the same angle of turning. Upon projecting the three levers 3,a,b,c into a plane together with a hypothetical line extending to the primary point A to the focus F one obtains a parallelogram, as is shown in FIG. 2b in an exemplary fashion. The FIG. 2b shows (in comparison with FIG. 2a) that the pivot axis A of lever 3a and ring R runs through the axis FA (on which is situated the invariance point F). The transducer TR provides motions about F in the same way lever 3a moves about hinge point and axis A in that the lever 3c remains parallel to lever 3a. This linkage can be obtained in a variety of ways.

FIG. 2b shows a particular example for the linking levers 3a and 3b; they are each divided respectively into two levers 3a and 3a'', and into levers 3b' and 3b'' to enforce a parallelogram partition between them. There is a second point of pivoting (lever 3c') which when projected onto axis FA is thus in line with F and A. The two levers 3a, 3a' and the two levers 3b', 3b'' together establish a linkage parallelogram that enforces parallelism between levers 3b' and 3b'' so that these levers in turn can enforce a parallel orientation of lever pairs 3a and lever 3c, to thereby make sure that these levers remain parallel to each other, so that, on the other hand invariance of the position and orientation of 3a,3b,3c and FA as a parallelogram obtains.

On the other hand lever 3c can be shifted together with the transducer TR in reference to and along the articulation of hinge points C. This way one can compensate the variable distance of the therapeutic focus F and the concrement in relation to the skin surface of the patient. The transducer TR on the other hand may be forced against the body of the patient by means of a spring in order to avoid uncontrolled movement and particularly any motion the patient undergoes or is subjected to with respect to the locating structure can be readily compensated. For selecting the scan plane transducer TR may be movable about its own axis, the locating mechanics can be fixed in every position through appropriate breaks.

Proceeding to the description of FIGS. 3a,b,c the locating procedure will be explained with reference to three different ultrasonic images. The image of FIG. 3a is a field wherein the focal point F is situated on the center axis TAX' of the imaging field. Visible off axis is a concrement, but the concrement is fairly close to the focus. The ultrasonic section plane can be selected through turning of the transducer TR around its own axis TA so that the stone on the concrement will be situated in that section plane as an initial procedure. In other words originally working but is visible in the section plane, but as the transducer is turned on its axis TA (seen on the monitor's screen as an image TA') the concrement image will appear.

FIG. 3b shows the concrement as imaged after positioning the relationship between the therapeutic head on one hand and the patient rest on the other hand in the z direction. This way then one was successful in placing the concrement into the level of the focus F. Now, the third image, FIG. 3c, illustrates how the concrement has been positioned in relation to point F following completed positioning. The concrement was placed into the therapeutic position to coincide with the focus F of the head TH, by shifting the patient rest in x and y directions which are horizontal directions of positioning.

SUMMARY OF POSITIONING

Head TH: this head has available three coordinate positions respectively in x,y and z axes. The vertical direction is represented by the axis z; a lengthwise horizontal displacement, representing particularly the regular resting positions of the patient, is represented by the axis x; and axis y extends transversely to the others.

In addition, the head TH can turn on an axis about and through an angle TH-omega so that the head's own axis FA delineates a cone; the surface of that cone has one line that is the vertical.

The transducer TR with its axis TA can turn about that axis through an angle US epsilon; head TR moreover can shift along that axis TA which is the motion USnu, head TR can also swivel up and down about the focus point F, by angle US phi; the ring R turns the head TR about axis FA and by an angle US omega.

The invention is not limited ot the embodiments described above but all changes and modifications thereof, not constituting departures from the spirit and scope of the invention, are intended to be included.

We claim:

1. In a lithotripter which includes a therapeutic head provided with a focusing source of shockwaves, for focusing shockwaves in an external focal point on a first axis, and an ultrasonic transducer for imaging an area in a patient in which shockwaves are to be focussed, the transducer having a second axis, the improvement comprising:
   a ring connected to the therapeutic head and being provided for movement around the center axis of the therapeutic head;
   movable means including a plurality of levers for connecting said transducer to said ring for obtaining movement of the transducer in relation to said head in isocentric relation to said external focal point of said therapeutic head, such that the first and second axes intersect in said focal point independently from a variable angular orientation of the axes to each other.

2. Apparatus as in claim 1 wherein said plurality of levers includes a pair of levers interconnected to maintain parallel position in relation to each other and wherein one of the levers so arranged is connected to the ring and the other one of the levers is connected to the transducer.

3. A lithotripter as in claim 1 wherein said movable means includes means for moving the transducer along said axis without change of isocentricity.

4. A lithotripter as in claim 1 wherein said movable means includes means for turning the transducer around said second axis.

5. In a lithotripter including a therapeutic shockwave generating and focussing head, for focussing shockwaves in an external focal point, further including an ultrasonic imaging transducer, the improvement comprising:

the head having a first axis, the transducer having a second axis;

a ring mounted to the head for rotation about the first axis;

articulated lever means for connecting the transducer to the ring so that the axes intersect in the focal point independently (a) from any angle between the axes;

(b) from rotation of the transducer about the axis of the head;

(c) from longitudinal shift of the transducer along its own axis towards and away from the focal point; and (d) from turning of the transducer about its own axis, so as to maintain a condition of isocentricity of orientation of the transducer relative to the focal point.

* * * * *